(12) United States Patent
Dann et al.

(10) Patent No.: US 11,007,151 B2
(45) Date of Patent: *May 18, 2021

(54) SPRAYABLE COMPOSITION CONTAINING ZINC OXIDE AND A FLUORO-OLEFIN PROPELLANT

(71) Applicant: Mission Pharmacal Company, San Antonio, TX (US)

(72) Inventors: Thomas Dann, Oldsmar, FL (US); Renee Nelson, Brandon, FL (US); Brian Wagner, Henderson, NV (US); Mary Walter, Vancouver, WA (US)

(73) Assignee: Mission Pharmacal Company, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/619,094

(22) Filed: Feb. 11, 2015

(65) Prior Publication Data
US 2015/0231071 A1 Aug. 20, 2015

Related U.S. Application Data

(60) Provisional application No. 61/939,826, filed on Feb. 14, 2014.

(51) Int. Cl.
| | | |
|---|---|---|
| *A61K 9/12* | (2006.01) | |
| *A61K 33/30* | (2006.01) | |
| *A61K 9/00* | (2006.01) | |
| *A61K 47/06* | (2006.01) | |
| *A61K 47/10* | (2017.01) | |
| *A61K 47/26* | (2006.01) | |
| *A61K 47/24* | (2006.01) | |

(52) U.S. Cl.
CPC ............ *A61K 9/124* (2013.01); *A61K 9/0014* (2013.01); *A61K 33/30* (2013.01); *A61K 47/10* (2013.01); *A61K 47/24* (2013.01); *A61K 47/26* (2013.01)

(58) Field of Classification Search
None
See application file for complete search history.

(56) References Cited

U.S. PATENT DOCUMENTS

| | | |
|---|---|---|
| 3,770,648 A | 11/1973 | Mackles |
| 4,981,677 A | 1/1991 | Thau |
| 5,143,288 A | 9/1992 | Kohler et al. |
| 5,286,475 A | 2/1994 | Louvet et al. |
| 5,665,368 A * | 9/1997 | Lentini ............... A61K 8/046 424/401 |
| 5,871,756 A | 2/1999 | Jeffcoat et al. |
| 6,047,946 A | 4/2000 | Kolanus |
| 6,165,450 A | 12/2000 | Chaudhuri et al. |
| 6,345,775 B1 | 2/2002 | Purvis, II et al. |
| 6,394,321 B1 | 5/2002 | Bayer |
| 6,627,178 B1 | 9/2003 | Cawthon |
| 6,949,249 B2 | 9/2005 | Healy et al. |
| 7,241,805 B2 | 7/2007 | Oberegger et al. |
| 8,087,548 B2 | 1/2012 | Kimball |
| 8,148,318 B2 | 4/2012 | Song et al. |
| 8,440,171 B2 | 5/2013 | Valpey, III et al. |
| 8,465,728 B2 | 6/2013 | Tasz et al. |
| 2004/0166073 A1 | 8/2004 | Darkwa et al. |
| 2004/0184992 A1 | 9/2004 | Abram |
| 2005/0244342 A1 | 11/2005 | Friedman et al. |
| 2005/0255048 A1 | 11/2005 | Hirsh et al. |
| 2006/0034937 A1 | 2/2006 | Patel |
| 2006/0165603 A1 | 7/2006 | Meakin et al. |
| 2008/0031907 A1 | 2/2008 | Tamarkin et al. |
| 2008/0152681 A1 | 6/2008 | Brown et al. |
| 2008/0194494 A1 | 8/2008 | Martinez et al. |
| 2009/0062171 A1 | 3/2009 | Song et al. |
| 2009/0257957 A1 | 10/2009 | Burnier et al. |
| 2011/0014135 A1 | 1/2011 | Buchta et al. |
| 2011/0150792 A1 | 6/2011 | Shao et al. |
| 2011/0240683 A1 | 10/2011 | Stegeman |
| 2012/0058973 A1 | 3/2012 | Narasimhan et al. |
| 2012/0219634 A1 | 8/2012 | Maslowski et al. |
| 2013/0058985 A1 | 3/2013 | Willems et al. |
| 2013/0078191 A1 | 3/2013 | Teramoto et al. |

(Continued)

FOREIGN PATENT DOCUMENTS

| | | |
|---|---|---|
| CA | 1088428 | 10/2008 |
| EP | 0 531 044 A1 | 3/1993 |

(Continued)

OTHER PUBLICATIONS

Honeywell. <https://www.honeywell-solstice-propellants.com/ResourceCenter/Documents/Honeywell-HFO1234ze-HFC-134a-physical-properties-comparison-table.pdf>; available Jun. 19, 2012; accessed Feb. 23, 2016.*
Evonik. Isolan GPS < http://glenncorp.com/wp-content/uploads/2013/11/DS_ISOLAN_GPS_e.pdf> accessed Jul. 3, 2017.*
Honeywell HFO-1234ze Blowing Agent < https://www51.honeywell.com/sm/lgwp-fr/common/documents/FP_LGWP_FR_Honeywell-HFO-1234ze_Literature_document.pdf> available Oct. 2008; accessed Nov. 25, 2018 (Year: 2008).*
English translation of KR 100820074 B1 (Year: 2008).*
Abstract and Machine Translation of JP2000128773, May 9, 2000, 7 pages.

(Continued)

*Primary Examiner* — Nicole P Babson
(74) *Attorney, Agent, or Firm* — Dority & Manning, P.A.

(57) ABSTRACT

A sprayable zinc oxide composition is provided. The sprayable zinc oxide composition can be used in the treatment of various skin conditions. The sprayable zinc oxide composition includes zinc oxide particles and a fluoro-olefin propellant. The present inventors have found that by selecting a propellant having a certain specific gravity, vapor pressure, and molecular weight, and by controlling the viscosity of the various components of the composition, the resulting zinc oxide composition resists settling such that a substantially homogeneous distribution of zinc oxide particles is maintained and can be evenly sprayed onto a surface without running once applied.

32 Claims, 4 Drawing Sheets

(56) References Cited

U.S. PATENT DOCUMENTS

| | | | |
|---|---|---|---|
| 2013/0115173 A1 | 5/2013 | Trumbore et al. | |
| 2013/0164226 A1 | 6/2013 | Nakamoto | |
| 2013/0233310 A1 | 9/2013 | Hilgers et al. | |
| 2013/0237613 A1 | 9/2013 | Kim | |
| 2013/0251644 A1 | 9/2013 | Majhi et al. | |
| 2013/0303615 A1 | 11/2013 | Scholz et al. | |
| 2014/0243299 A1* | 8/2014 | Gurge | A61K 9/122 514/179 |
| 2015/0231072 A1 | 8/2015 | Dann et al. | |
| 2015/0232260 A1 | 8/2015 | Dann et al. | |

FOREIGN PATENT DOCUMENTS

| | | |
|---|---|---|
| EP | 0 937 451 A2 | 8/1999 |
| JP | 2006213409 A | 8/2006 |
| JP | 2012197359 A | 10/2012 |
| KR | 100820074 B1 * | 4/2008 |
| WO | WO 2004/037225 A2 | 5/2004 |
| WO | WO 2007/039825 A2 | 4/2007 |
| WO | WO 2008/002428 A1 | 1/2008 |
| WO | WO 2012/014732 A1 | 2/2012 |
| WO | WO 2013/067271 A2 | 5/2013 |
| WO | WO 2013/142249 A1 | 9/2013 |

OTHER PUBLICATIONS

International Search Report and Written Opinion for PCT/US2015/015315 dated May 14, 2015. 9 pages.

Philip Haw, "The HLB System. A Time Saving Guide to Surfactant Selection", Presentation to the Midwest chapter of the society of Cosmetic Chemists, Mar. 9, 2004, 39 pages.

* cited by examiner

SPRAYABLE COMPOSITION CONTAINING ZINC OXIDE AND A FLUORO-OLEFIN PROPELLANT

RELATED APPLICATION

The present application claims priority to U.S. Provisional Application Ser. No. 61/939,826, filed on Feb. 14, 2014, which is incorporated herein in its entirety by reference thereto.

BACKGROUND OF THE INVENTION

Much of the population has experienced a skin condition such as a rash, pressure ulcer, or a wound such as a cut or first degree burn, that has required topical application of a cream or ointment to assist in the healing process. Often, these conditions are more prevalent in infants, the elderly, and infirm. For instance, infants, the elderly, and infirm can be susceptible to developing incontinent dermatitis, which occurs when the skin is exposed to prolonged wetness, increased skin pH caused due to contact with urine and feces, and the resulting breakdown of the stratum corneum, or the outermost layer of the skin. Meanwhile, pressure ulcers, also known as decubitus ulcers or bedsores, are also a concern. Pressure ulcers are localized injuries to the skin and/or underlying tissue that usually occur over a bony prominence as a result of pressure, or pressure in combination with shear and/or friction. The most common sites are the sacrum, coccyx, heels or the hips, but other sites such as the elbows, knees, ankles or the back of the cranium can be affected. Pressure ulcers occur due to pressure applied to soft tissue resulting in completely or partially obstructed blood flow to the soft tissue. Factors that can contribute to the formation of ulcers include protein-calorie malnutrition, microclimate (skin wetness caused by sweating or incontinence), diseases that reduce blood flow to the skin, such as arteriosclerosis, or diseases that reduce the sensation in the skin, such as paralysis or neuropathy.

The aforementioned conditions, and other skin conditions, can be prevented or treated, for instance, by the application of zinc oxide to the affected area of the skin. Zinc oxide can help speed up the wound healing process and can also limit the skin's exposure to excessive moisture. As such, one approach for treating these skin conditions is to block moisture from reaching the skin, such as by the application of oil-based protectants or barrier creams, including various over-the-counter creams or ointments containing zinc oxide, to the affected area. However, if the skin is not thoroughly dry, some of these oil-based protectants and creams can actually seal the moisture inside the skin rather than outside the skin. Further, such protectants and creams are very viscous and can be greasy, resulting in difficulty in removing the protectants and creams from one's hands after application onto the affected area of the skin. In addition, rubbing these products into the skin can cause additional discomfort or pain, and in the event that a caretaker or healthcare provider must apply the product to a patient, this could lead to embarrassment for both the patient and caretaker depending on the location of application.

As such, a need exists for a composition that can provide a sufficient moisture barrier without the risk of sealing moisture inside the skin and that can be more easily applied without causing discomfort. One approach is to use a treatment composition in conjunction with a propellant to create an aerosol spray composition. However, the high viscosity of the resulting aerosol spray composition means that it is often difficult to formulate the composition into a medium that can be sprayed due to issues with clogging of the valves and nozzle in the dispenser. Further, many propellants have too high of a vapor pressure, which could result in an erratic spray or stream of product that is not evenly controlled, meaning that applying a smooth, even coating of the aerosol spray composition to the area of the skin requiring treatment cannot be achieved.

Still another problem associated with the aforementioned sprayable compositions is that the particulate ingredients of the sprayable compositions, such as zinc oxide, often settles to the bottom of the container in which the sprayable composition is stored, resulting in settling of the composition and caking of the product in the container. In addition, many sprayable compositions have a low viscosity to allow for spraying, but this results in compositions that are not viscous enough when applied to the skin's surface, resulting in a runny product that does not evenly coat or effectively contact the skin.

As such, a need exists for a sprayable zinc oxide composition containing zinc oxide particles that remain substantially homogeneously distributed and that can be evenly sprayed onto the skin as a fine mist.

SUMMARY OF THE INVENTION

In accordance with one embodiment of the present invention, a sprayable zinc oxide composition is disclosed. The composition includes a fluoro-olefin propellant and zinc oxide particles.

In accordance with another embodiment of the present invention, a method of forming a sprayable zinc oxide composition is disclosed. The method includes forming a base zinc oxide composition, wherein the base zinc oxide composition includes zinc oxide particles and a carrier fluid; introducing the base zinc oxide composition into a spray container; and injecting a hydrofluoro-olefin propellant into the container.

In accordance with yet another embodiment of the present invention, a method of applying a zinc oxide composition to a surface is disclosed. The method includes spraying the composition onto the surface to leave a coating thereon, wherein the composition includes a fluoro-olefin propellant and zinc oxide particles.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figure, in which.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention.

Generally speaking, the present invention is directed to a sprayable composition that can be used in the treatment of a skin condition. The composition includes a propellant particularly useful for forming a sprayable composition that includes zinc oxide particles. The propellant can, for instance, be a hydrofluoro-olefin propellant. The present inventors have found that by selectively controlling certain aspects of the propellant, such as the specific gravity, vapor pressure, and/or molecular weight, a composition having a substantially homogeneous distribution of zinc oxide particles can be achieved. Further, the sprayable composition can be stable such that less than about 3 wt. %, such HFO-1234ze (specific gravity of 1.17 at 21° C.), in the cis- and/or trans-forms. It should be understood that HFO-1234ze refers to 1,1,1,3-tetrafluoropropene, independent of whether it is the cis- or trans-form, and the terms "cisHFO-1234ze" and "transHFO-1234ze" are used herein to describe the cis- and trans-forms of 1,1,1,3-tetrafluoropropene, respectively.

In some embodiments, the HFO-1234ze can include a combination of transHFO-1234ze and cisHFO-1234ze, such as from about 90% to about 99% trans-isomer on the basis of total HFO-1234ze, with the cis-isomer comprising from about 1% to about 10% of the same basis. As such, in some embodiments, the propellant of the present invention can include a combination of cisHFO-1234ze and transHFO-1234ze, preferably in a cis- to trans-weight ratio of from about 1:99 to about 10:99, such as from about 1:99 to about 5:95, such as from about 1:99 to about 3:97.

Although the properties of cisHFO-1234ze and transHFO-1234ze differ in at least some respects, it is contemplated that each of these compounds is adaptable for use, either alone or together with other compounds including its stereoisomer, as a propellant in the sprayable zinc oxide composition of the present invention. For example, while transHFO-1234ze has a relatively low boiling point (−19° C.), it is nevertheless contemplated that cisHFO-1234ze, with a boiling point of 9° C., can also be used as a propellant in the sprayable zinc oxide composition of the present invention. Further, it is to be understood that the terms HFO-1234ze and 1,1,1,3-tetrafluoropropene refer to both stereo isomers, and the use of these terms covers both the cis- and trans-forms.

The amount of the fluoro-olefin propellant contained in the sprayable zinc oxide composition of the present invention can range from about 5 wt. % to about 95 wt. %, such as from 10 wt. % to about 80 wt. %, such as from about 15 wt. % to about 60 wt. % based on the total weight of the composition.

b. Zinc Oxide Particles

Additional components that can be present in the sprayable zinc oxide composition will now be discussed in more detail. First, the sprayable zinc oxide composition of the present invention further includes zinc oxide particles, which repel moisture and create a barrier between the skin and environment to protect the skin from excessive moisture. The zinc oxide particles can have an average particle size of from about 20 nanometers to about 200 nanometers, such as from about 25 nanometers to about 150 nanometers, such as from about 30 nanometers to about 100 nanometers.

The zinc oxide particles can be hydrophobic, for example, by application of a hydrophobic coating on the surface of the zinc oxide particles, as described in more detail below. The particles can also carry an inorganic coating, separately or in combination with the hydrophobic coating, as described in more detail below. The zinc oxide particles may be coated with alumina, silica, an organic material, silicones, or combinations thereof. Other suitable surface treatments may include: phosphate esters (including lecithins), perfluoroalkyl alcohol phosphates, fluorosilanes, isopropyl titanium triisostearate, stearic or other fatty acids, silanes, dimethicone and related silicone polymers, or combinations thereof.

For example, zinc oxide particles may be coated with oxides of other elements such as oxides of aluminum, zirconium or silicon, or mixtures thereof such as alumina and silica. Alternatively, the zinc oxide particles may be treated with boron nitride or other known inorganic coatings, singly or in combinations before incorporation into the voids of the particulate. The inorganic coating may be applied using techniques known in the art. A typical process can include forming an aqueous dispersion of zinc oxide particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali, as appropriate. The inorganic coating, if present, can be applied as a first layer to the surface of the zinc oxide particles.

In another embodiment, the zinc oxide particles can include an organic coating that provides hydrophobicity. The organic coating can be applied to the inorganic coating, if present, or directly to the zinc oxide. The hydrophobic coating agent may be, for example, a silicone, a silane, a metal soap, a titanate, an organic wax, or combinations thereof. The hydrophobic coating can alternatively include a fatty acid, for example, a fatty acid containing 10 to 20 carbon atoms, such as lauric acid, stearic acid, isostearic acid, and salts of these fatty acids. The fatty acid may be isopropyl titanium trisostearate. With respect to the silicone, the hydrophobic coating may be a methicone, a dimethicone, their copolymers or mixtures thereof. The silicone may also be an organosilicon compound, for example dimethylpolysiloxanes having a backbone of repeating -Me$_2$SiO— units ("Me" is methyl, CH$_3$), methyl hydrogen polysiloxanes having a backbone of repeating -MeHSiO— units and alkoxysilanes of formula R$_n$OSiH$_{(4-n)}$ where "R" is alkyl and "n" is the integer 1, 2 or 3. With respect to the silane, the hydrophobic coating agent may be an alkoxysilanes, for example an alkyltriethoxy or an alkyltrimethoxy silanes available from OSI Specialties or PCR. The alkoxysilane may be a triethoxycaprylylsilane or a perfluoroalkylethyl triethoxysilane having a C$_3$ to C$_{12}$ alkyl group that is straight or branched. Zinc oxide particles with a triethoxycaprylylsilane coating are commercially available under the name ZANO™ 10 Plus from Umicore Zinc Chemicals.

The amount of zinc oxide particles contained in the sprayable zinc oxide composition of the present invention can range from about 0.5 wt. % to about 30 wt. %, such as from 1 wt. % to about 25 wt. %, such as from about 2 wt. % to about 20 wt. % based on the total weight of the sprayable zinc oxide composition.

c. Carrier Fluid

The propellant and zinc oxide particles can each be substantially homogeneously distributed in a carrier fluid as part of a solution or as components in a colloidal suspension or dispersion. For instance, the propellant, zinc oxide particles, and carrier fluid can form a water-in-oil emulsion or an oil-in-water emulsion. It is also to be understood, however, that the carrier fluid can be oil or water.

Suitable oils that can be used in the carrier fluid include mineral oils, plant-based oils, silicone oils, or a combination thereof. Examples of commercially available mineral oils, which are liquid petroleum derivatives that may be used in accordance with the present invention can include Witco Corporation's CARNATION™ mineral oil or Penreco Corporation's DRAKEOL™ mineral oil. Suitable plant-based oils, which are non-petroleum biomass derived oils, that can be used include vegetable or fruit oils, such as almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppy seed oil, pine oil, castor oil, soybean oil, avocado oil, safflower oil, coconut oil, hazelnut oil, olive oil, grape seed oil, sunflower oil, apricot kernel oil, geranium oil, rice bran oil and mixtures thereof. Silicone oils that can be used include disiloxane, cyclomethicone, dimethicone and derivatives thereof, and polydimethylsiloxane fluids. Cyclomethicone is a volatile compound and evaporates when applied to the skin's surface, such that the resulting coating is drier to the touch. Other similar volatile compounds that can be used include isododecane.

Water can also be used as a carrier fluid either alone or in conjunction with any of the oils described above as part of a water-in-oil emulsion or an oil-in-water emulsion. It is of course not intended that the carrier fluid be limited to the materials described above.

When both an oil and water are utilized, the oil can be present in the composition in an amount ranging from about 1 wt. % to about 35 wt. %, such as from about 3 wt. % to about 30 wt. %, such as from about 5 wt. % to about 25 wt. % based on the total weight of the composition. Meanwhile, the water can be present in an amount less than about 50 wt. %, such as an amount ranging from about 1 wt. % to about 50 wt. %, such as from about 5 wt. % to about 45 wt. %, such as from about 10 wt. % to about 40 wt. % based on the total weight of the composition. Further, in some embodiments, it should be understood that the water is present in an amount less than 30 wt. % based on the total weight of the composition.

Regardless of the particular carrier fluid or combination of carrier fluids utilized, the total amount of the carrier fluid or fluids present in the composition can range from about 10 wt. % to about 70 wt. %, such as from about 15 wt. % to about 65 wt. %, such as from about 20 wt. % to about 60 wt. % based on the total weight of the composition.

d. Emulsifiers

The sprayable zinc oxide composition can also include one or more emulsifiers as part of an emulsifier system to help create a stable, substantially homogeneous, uniform dispersion of the propellant and the zinc oxide particles by preventing the separation of the sprayable zinc oxide composition into constituent phases. The emulsifier system may include one or more nonionic, anionic, and/or amphoteric emulsifiers, including mixtures containing different species or mixtures of different surfactants within the same species.

Nonionic surfactants, which typically have a hydrophobic base (e.g., long chain alkyl group or an alkylated aryl group) and a hydrophilic chain (e.g., chain containing ethoxy and/or propoxy moieties), can be particularly suitable. Some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglycerides, or diglycerides of long chain alcohols, and mixtures thereof. Particularly suitable nonionic emulsifiers may include ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid esters (e.g., sold under the trade name TWEEN®), and sorbitan fatty acid esters (e.g., sold under the trade name SPAN™ or ARLACEL®), etc. The fatty components used to form such emulsifiers may be saturated or unsaturated, substituted or unsubstituted, and may contain from 6 to 22 carbon atoms, in some embodiments from 8 to 18 carbon atoms, and in some embodiments, from 12 to 14 carbon atoms.

Although any emulsifier may generally be employed, the present inventors have discovered that a certain combination of hydrophilic and lipophilic nonionic emulsifiers is particularly effective in stabilizing the emulsion. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. Desirably, the emulsion of the present invention can include at least one "hydrophilic" emulsifier that has an HLB value of from about 10 to about 20, in some embodiments from about 12 to about 19, and in some embodiments, from about 14 to about 18. Likewise, the emulsion can also include at least one "lipophilic" emulsifier that has an HLB value of from about 0.5 to about 10, in some embodiments from about 1 to about 9, and in some embodiments, from about 2 to about 8. If desired, two or more surfactants may be employed that have HLB values either below or above the desired value, but together have an average HLB value within the desired range. Regardless, the present inventors have discovered that the weight ratio of lipophilic emulsifiers to hydrophilic emulsifiers in the sprayable zinc oxide composition is typically within a range of from about 5 to about 30, in some embodiments from about 7.5 to about 25, and in some embodiments, from about 10 to about 20. Further, the present inventors have discovered that the overall HLB value of the sprayable zinc oxide composition is generally lipophilic and ranges from about 3 to about 10, such as from about 4 to about 9, such as from about 5 to about 8.

One particularly useful group of "lipophilic" emulsifiers are sorbitan fatty acid esters (e.g., monoesters, diester, triesters, etc.) prepared by the dehydration of sorbitol to give 1,4-sorbitan, which is then reacted with one or more equivalents of a fatty acid. The fatty-acid substituted moiety can be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. Such surfactants are commercially available under the name SPAN™ or ARLACEL™, usually with a letter or number designation which distinguishes between the various mono-, di- and triester substituted sorbitans. SPAN™ and ARLACEL™ surfactants are lipophilic and are generally soluble or dispersible in oil, but not generally soluble in water. One particularly suitable surfactant is sorbitan oleate, which is commercially available as SPAN™ 80. Generally these surfactants will have HLB value in the range of 1.8 to 8.6.

Other useful lipophilic emulsifiers that can be used can include, for example, silicone water-in-oil emulsifiers. By silicone it is meant a molecule that includes at least one siloxane (—Si—O—) repeating unit and further includes a hydrophobic moiety and a hydrophilic moiety. The HLB value of the silicone water-in-oil emulsifier is relatively low. For example, in some embodiments, the silicone emulsifier can have an HLB value in the range of 2 to 9.

Examples of suitable silicone water-in-oil emulsifiers can include non-crosslinked dimethicone copolyols such as alkoxy dimethicone copolyols, silicones having pendant hydrophilic moieties such as linear silicones having pendant polyether groups, branched polyether and alkyl modified silicones, branched polyglycerin and alkyl modified silicones, and combinations thereof. Examples of commercially available non-crosslinked dimethicone copolyols include the following from Dow Corning of Midland, Mich.: cyclopentasiloxane and PEG/PPG-18/18 dimethicone available as DC 5225C, and cyclopentasiloxane and PEG-12 dimethicone crosspolymer available as DC9011. Certain non-crosslinked dimethicone copolyols are cetyl dimethicone copolyols such as cetyl PEG/PPG-10/1 dimethicone sold under the name ABIL™ EM-90, branched polyether and alkyl modified silicones such as lauryl PEG-9 polydimethylsiloxyethyl dimethicone sold under the name KF-6038, and branched polyglycerin and alkyl modified silicones such as lauryl polyglyceryl-3 polydimethylsiloxyethyl dimethicone sold under the name KF-6105. Other non-crosslinked dimethicone copolyols include, for example, bis-PEG/PPG-14/dimethicone copolyol sold under the name ABIL™ EM-97 and the polyglyceryl-4 isostearate/cetyl dimethicone copolyol/hexyl laurate mixture sold under the name ABIL™ WE 09. ABIL™ EM-90, ABIL™ EM-97, and ABIL™ WE 09 are available from Evonik Goldschmidt GmbH of Essen, Germany. KF-6038 are KF-6105 are available from Shin-Etsu Silicones of Akron, Ohio. One particularly suitable emulsifier for use in the present invention is ABIL™ WE 09, which has an HLB value of about 5. Another particularly suitable emulsifier is ABIL™ EM 90, which also has an HLB value of about 5.

Still another suitable nonionic lipophilic emulsifier that can be included in the sprayable zinc oxide composition of the present invention is octyldodecanol/octyldechyl xyloside/PEG-30, which is commercially available from Seppic S.A. under the name EASYNOV™.

Meanwhile, sorbitan fatty acid esters (e.g., monoesters, diester, triesters, etc.) that have been modified with polyoxyethylene are likewise a particularly useful group of "hydrophilic" emulsifiers. These materials are typically prepared through the addition of ethylene oxide to a 1,4-sorbitan ester. The addition of polyoxyethylene converts the lipophilic sorbitan ester surfactant to a hydrophilic surfactant that is generally soluble or dispersible in water. Such materials are commercially available under the designation TWEEN™ (e.g., TWEEN™ 80, polysorbate 80, or polyethylene (20) sorbitan monooleate). TWEEN™ surfactants generally have a HLB value in the range of 9.6 to 16.7. For instance TWEEN™ 80 has an HLB value of 15. Still other suitable hydrophilic emulsifiers can include sucrose fatty acid esters, such as saccharose monopalmitate (HLB of 15) and saccharose monostearate (HLB of 11), or PEG-32 glyceryl laurate (HLB of 14), as well as polyethylene glycol (PEG) n-alkanol esters of the BRIJ™ family such as BRIJ™ 35, 56, 58, 76, 78, and 99, which have an HLB in the range 0112.4 to 16.9. BRIJ™ 56 is polyoxyethylene[10] cetyl ether, for example, has an HLB value of 12.9.

Regardless of the particular emulsifiers utilized, the emulsifiers can be present in the sprayable zinc oxide composition in an amount ranging from about 0.1 wt. % to about 20 wt. %, such as from about 0.5 wt. % to about 15 wt. %, such as from about 1 wt. % to about 10 wt. % based on the total weight of the sprayable zinc oxide composition. Further, the present inventors have discovered that the weight ratio of lipophilic emulsifiers to hydrophilic emulsifiers in the sprayable zinc oxide composition is typically within a range of from about 5 to about 30, in some embodiments from about 7.5 to about 25, and in some embodiments, from about 10 to about 20.

e. Viscosity Modifier

In addition, the composition can include one or more viscosity modifiers which can also help to prevent the separation of the various components of the composition. For instance, in some embodiments, such as when the carrier fluid includes more than one component, one or more viscosity modifiers can be added to the oil phase or the water phase of an emulsion to adjust the viscosity such that separate components in the composition are more miscible. Further, the viscosity of the overall composition can be adjusted so that it is not so high that the composition cannot be sprayed onto a surface, but it is not so low that the composition is too runny such that it does not evenly coat the surface. As such, the composition can have a viscosity greater than about 1000 centipoise, such as from about 1000 centipoise to about 8000 centipoise, such as from about 1500 centipoise to about 6000 centipoise, such as from about 2000 centipoise to about 4000 centipoise.

When a water-in-oil emulsion or an oil-in-water emulsion is utilized in the sprayable zinc oxide composition, the one or more viscosity modifiers can be added to the water phase of the water-in-oil emulsion or the oil-in-water emulsion to enhance the miscibility between the water phase and the oil phase, which promotes the substantially homogeneous distribution of the components of the sprayable zinc oxide composition. It is also to be understood, however, that the viscosity modifier can be added to an already-formed oil-in-water or water-in-oil emulsion to adjust the viscosity as needed.

Suitable viscosity modifiers include carboxylic acid polymers which are crosslinked compounds containing one or more monomers derived from acrylic acid, substituted acrylic acids, and salts and derivatives of these acrylic acids and substituted acrylic acids. They can be crosslinked homopolymers of an acrylic acid or of a derivative thereof, such as acrylamidopropylsulfonic acid. They can be also crosslinked copolymers having (i) a first monomer selected from the group consisting of (meth)acrylic acid, derivatives thereof, short chain (i.e., $C_1$-$C_4$) acrylate ester monomers, and mixtures thereof, and (ii) a second monomer which is a long chain (i.e., $C_8$-$C_{40}$) substituted polyethylene glycol acrylate ester monomer.

Examples of commercially available carboxylic acid polymers include CARBOPOL™ 1342, PEMULEN™ TR-1, and PEMULEN™ TR-2 available from Lubrizol Corp.; Sepigel 305, SIMULGEL™ EG, SIMULGEL™ NS, and SIMULGEL™ 600, available from Seppic S.A.; VISCOLAM™ AT100P and VISCOLAM™ AT64/P, available from Lamberti S.p.A. One commercially available viscosity modifier is available from Seppic S.A. as SIMULGEL™ NS. SIMULGEL™ NS includes a hydroxyethyl acrylate/sodium acryloyldimethyl taurate copolymer, squalane, and polysorbate 60, which can be added to an oil phase of a water-in-oil or oil-in-water emulsion.

Other suitable viscosity modifiers that can be used include cornstarch (topical starch), talc, rice starch, oat starch, tapioca starch, potato starch, legume starches, soy starch, turnip starch, microcrystalline cellulose, kaolin, aluminum starch octenyl succinate, and mixtures thereof. Water soluble aluminum starch octenyl succinates are commercially available from National Starch & Chemical Co. as DRY FLO™ Pure, DRY FLO™ XT, DRY FLO™ PC, and/or DRY FLO™ AF (aluminum free grade) and are water soluble such that they can be included in a water phase of a water-in-oil emulsion or an oil-in-water emulsion.

Regardless of the particular viscosity modifiers utilized, the viscosity modifier can be present in the sprayable zinc oxide composition in an amount ranging from about 0.05 wt.

% to about 15 wt. %, such as from about 0.1 wt. % to about 10 wt. %, such as from about 0.5 wt. % to about 5 wt. % based on the total weight of the sprayable zinc oxide composition.

f. Additional Moisture Brier/Repellant Materials

The sprayable zinc oxide composition can also include other moisture barrier or repellant materials in addition to the zinc oxide particles discussed above. For example, the sprayable zinc oxide composition can include paraffin, microcrystalline wax, petrolatum, beeswax, or a combination thereof. Such moisture repellant materials can be present in the sprayable zinc oxide composition in an amount ranging from about 0.1 wt. % to about 6 wt. %, such as from about 0.25 wt. % to about 4 wt. %, such as from about 0.5 wt. % to about 2 wt. % based on the total weight of the composition.

g. Conditioning Agents

The sprayable zinc oxide composition can further include one or more conditioning agents to help condition the skin. For example, the composition can include thymol iodide, sodium chloride, magnesium dichloride, magnesium sulfate, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols, ricinoleate, acetate of ethoxylated alcohols-esters, hydrogenolysis of lanolin, ethoxylated hydrogenated lanolin, ethoxylated sorbitol lanolin, or a combination thereof. Thymol iodide and magnesium sulfate may be particularly useful. One or more conditioning agents can be present in the sprayable zinc oxide composition in an amount ranging from about 0.05 wt. % to about 10 wt. %, such as from about 0.1 wt. % to about 7.5 wt. %, such as from about 0.5 wt. % to about 5 wt. % based on the total weight of the composition.

h. Additional Components

Other optional components in the sprayable zinc oxide composition can include skin care-additives such as emollients, as well as fragrances and preservatives. For instance, an emollient such as caprylic/capric triglyceride can be included in the sprayable zinc oxide composition. Other suitable emollients include stearoxy trimethyl silane, cetyl lactate, and alkyl lactate, such as $C_{12}$-$C_{15}$ alkyl lactate. When emollients are used, the sprayable zinc oxide composition can feel smooth to the touch when applied to the skin. One or more emollients can be present in the sprayable zinc oxide composition in an amount ranging from about 0.1 wt. % to about 25 wt. %, such as from about 0.5 wt. % to about 20 wt. %, such as from about 1 wt. % to about 15 wt. % based on the total weight of the composition.

Further, a fragrance can be present in the sprayable zinc oxide composition in an amount ranging from about 0.005 wt. % to about 2 wt. %, such as from about 0.01 wt. % to about 1.5 wt. %, such as from about 0.02 wt. % to about 1 wt. % based on the total weight of the composition.

Meanwhile, preservatives can be present in the composition in an amount ranging from about 0.01 wt. % to about 6 wt. %, such as from about 0.02 wt. % to about 4 wt. %, such as from about 0.05 wt. % to about 1 wt. % based on the total weight of the composition. Suitable preservatives include paraben-based preservatives such as methylparaben and propylparaben.

Further, the present inventors have found that a freezing point depressant can be included in the composition to limit the amount of crystallization of any solid components, which can then reduce or limit clogging of the composition when sprayed. If desired, one or more freezing point depressants may be employed, such as glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); and so forth. Such freezing point depressants can be present in the composition in an amount ranging from about 0.1 wt. % to about 15 wt. %, such as from about 0.5 wt. % to about 10 wt. %, such as from about 1 wt. % to about 5 wt. % based on the total weight of the composition.

II. Formation of the Sprayable Zinc Oxide Composition

Generally, the sprayable zinc oxide composition of the present invention can be made by forming a base zinc oxide composition from a carrier fluid and zinc oxide particles, introducing the base zinc oxide composition into a spray container, and injecting a propellant, such as a hydrofluoroolefin propellant, into the container. When the base zinc oxide composition is in the form of a water-in-oil emulsion or an oil-in-water emulsion, for example, the base zinc oxide composition can be made by first separately forming an oil phase and a water phase.

The manner in which the water-in-oil emulsion or the oil-in-water emulsion is formed may vary as is known to those skilled in the art. In one embodiment, for example, the oil can be initially blended with any optional emulsifiers, emollients, conditioning agents, etc. to form the oil phase. In such embodiments, the oil phase can contain oils in an amount of from about 30 wt. % to about 80 wt. %, such as from about 35 wt. % to about 70 wt. %, such as from about 40 wt. % to about 60 wt. % based on the total weight of the oil phase. Further, the oil phase can include emulsifiers in an amount ranging from about 5 wt. % to about 35 wt. %, such as from about 10 wt. % to about 30 wt. %, such as from about 15 wt. % to about 25 wt. % based on the total weight of the oil phase. The addition of the emulsifiers can result in an oil phase having an HLB value between about 6 and about 7. In addition, the oil phase can include emollients in an amount ranging from about 10 wt. % to about 45 wt. %, such as from about 15 wt. % to about 40 wt. %, such as from about 20 wt. % to about 35 wt. % based on the total weight of the oil phase. Moreover, the oil phase can include conditioning agents in an amount ranging from about 0.5 wt. % to about 10 wt. %, such as from about 1 wt. % to about 7.5 wt. %, such as from about 1.5 wt. % to about 5 wt. % based on the total weight of the oil phase.

Meanwhile, the water phase can be formed by blending water and other components, such as conditioning agents, viscosity modifiers, etc. In such embodiments, the water phase can include water in an amount ranging from about 50 wt. % to about 99 wt. %, such as from about 55 wt. % to about 98 wt. %, such as from about 60 wt. % to about 97 wt. %. The water phase can also include conditioning agents in an amount ranging from about 0.5 wt. % to about 15 wt. %, such as from about 1 wt. % to about 10 wt. %, such as from about 1.5 wt. % to about 7.5 wt. % based on the total weight of the water phase. Additionally, the water phase can include viscosity modifiers in an amount ranging from about 0.25 wt. % to about 10 wt. %, such as from about 0.5 wt. % to about 7.5 wt. %, such as from about 1 wt. % to about 5 wt. % based on the total weight of the water phase.

After the oil phase and water phase are separately formed, the water phase can be added to the oil phase to form a water-in-oil emulsion. The combination of the phases may be facilitated through agitation (e.g., stirring) and control of the temperatures of each mixture. Next, the zinc oxide particles can be added to the water-in-oil emulsion. The zinc oxide particles can be present in the water-in-oil emulsion in an amount ranging from about 0.25 wt. % to about 35 wt. %, such as from about 0.5 wt. % to about 30 wt. %, such as from about 1 wt. % to about 25 wt. %, such as from about 5 wt. % to about 15 wt. % based on the total weight of the base zinc oxide composition. Then, if desired, other components such as fragrances, preservatives, freezing point depressants, and additional viscosity modifiers can be added to the emulsion. Fragrances can be added in an amount ranging from about 0.01 wt % to about 5 wt. %, such as from about 0.05 wt. % to about 2.5 wt. %, such as from about 0.1 wt. % to about 1 wt. % based on the total weight of the base zinc oxide composition. Likewise, preservatives can be added in an amount ranging from about 0.01 wt. % to about 5 wt. %, such as from about 0.05 wt. % to about 2.5 wt. %, such as from about 0.1 wt. % to about 1 wt. % based on the total weight of the base zinc oxide composition. In addition, freezing point depressants can be added in an amount ranging from about 0.5 wt. % to about 15 wt. %, such as from about 1 wt. % to about 10 wt. %, such as from about 2 wt. % to about 8 wt. % based on the total weight of the base zinc oxide composition. Further, viscosity modifiers can be added in an amount ranging from about 0.1 wt. % to about 15 wt. %, such as from about 0.5 wt. % to about 10 wt. %, such as from about 1 wt. % to about 8 wt. % based on the total weight of the base zinc oxide composition. As such, it is to be understood that in some embodiments, a first viscosity modifier can be added during formation of the water phase, while a second viscosity modifier can be added after forming the emulsion by combining the water and oil phases to form the base zinc oxide composition.

Figure 1:
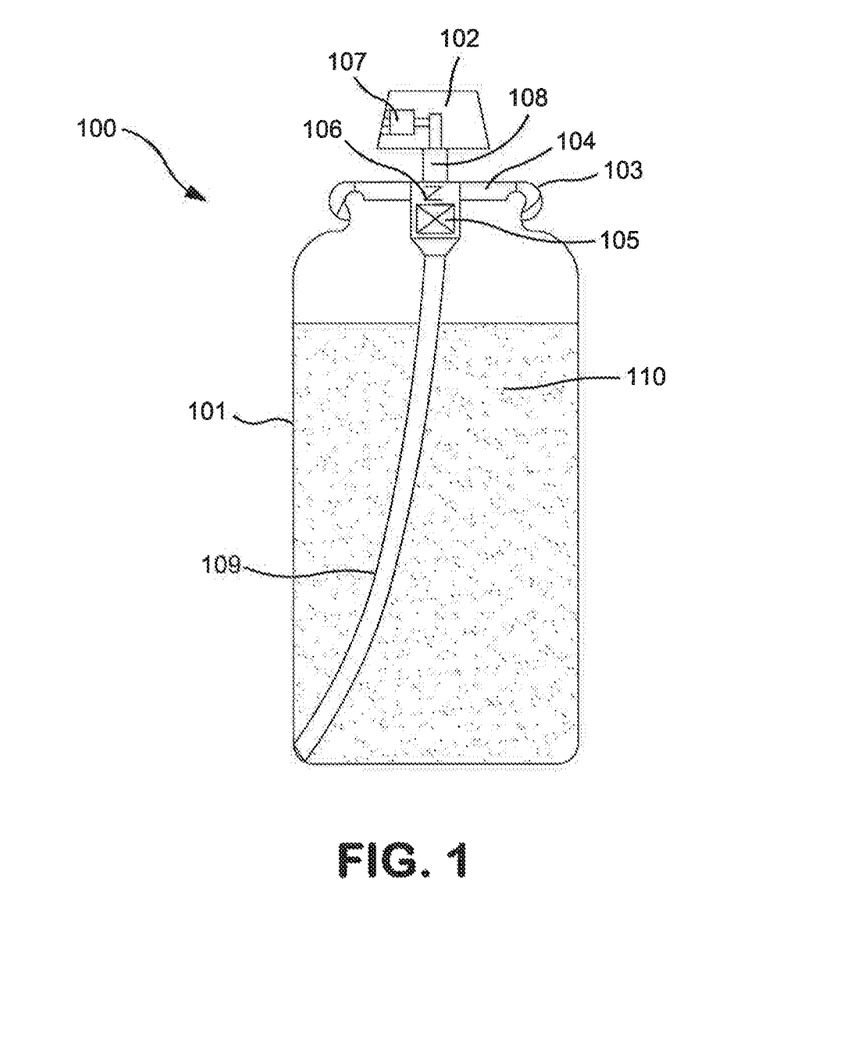
FIG. 1 is a cross-sectional side view of a spray delivery system according to one embodiment of the present disclosure.
Figure 2A:
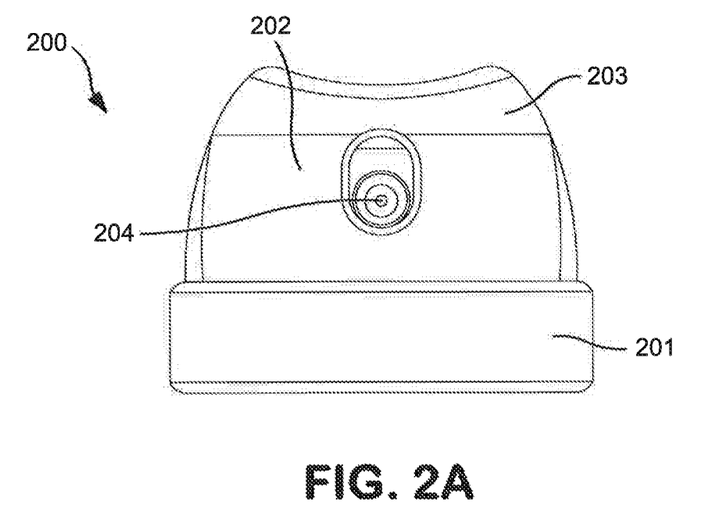
FIG. 2A is front view of an actuator that can be used in a spray delivery system according to one embodiment of the present disclosure.
Figure 2B:
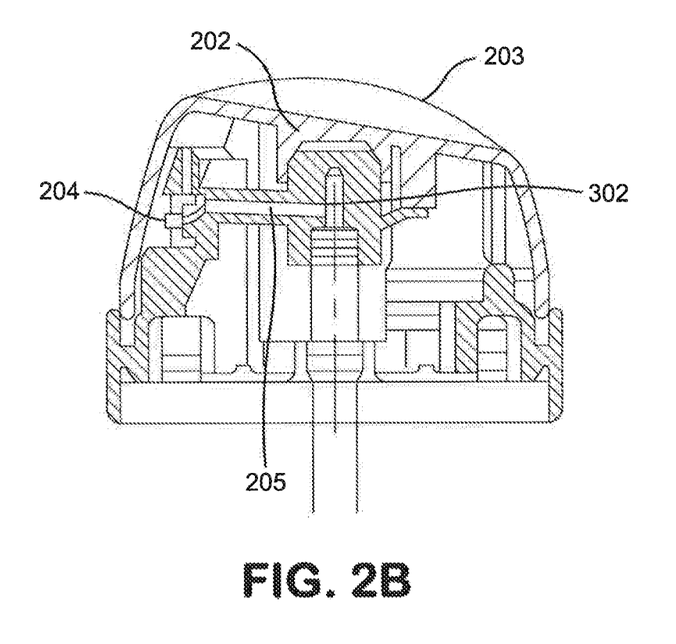
FIG. 2B is a cross-sectional side view of the actuator of FIG. 2A.
Figure 3:
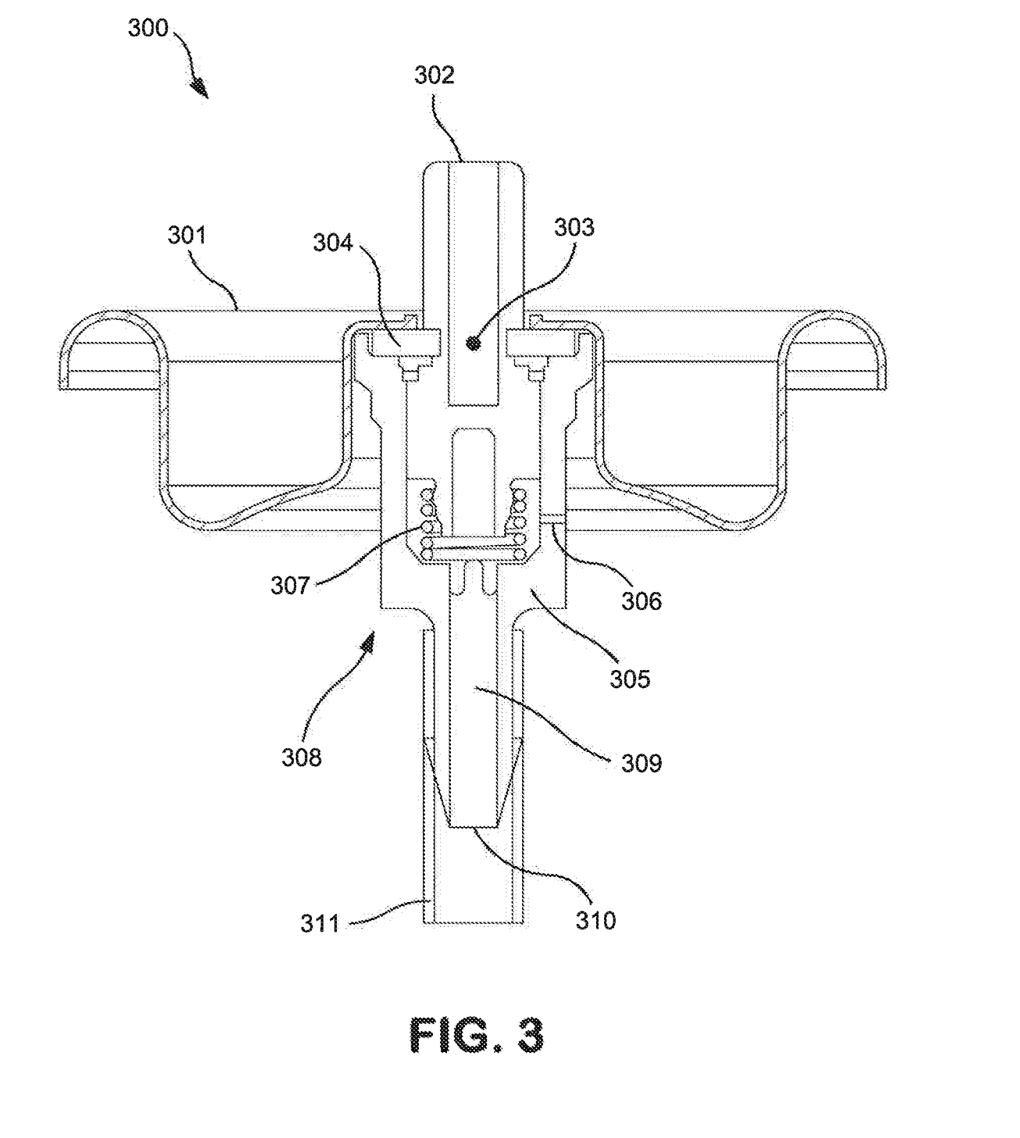
FIG. 3 is a cross-sectional side view of a spray assembly according to one embodiment of the present disclosure.
Figure 4:
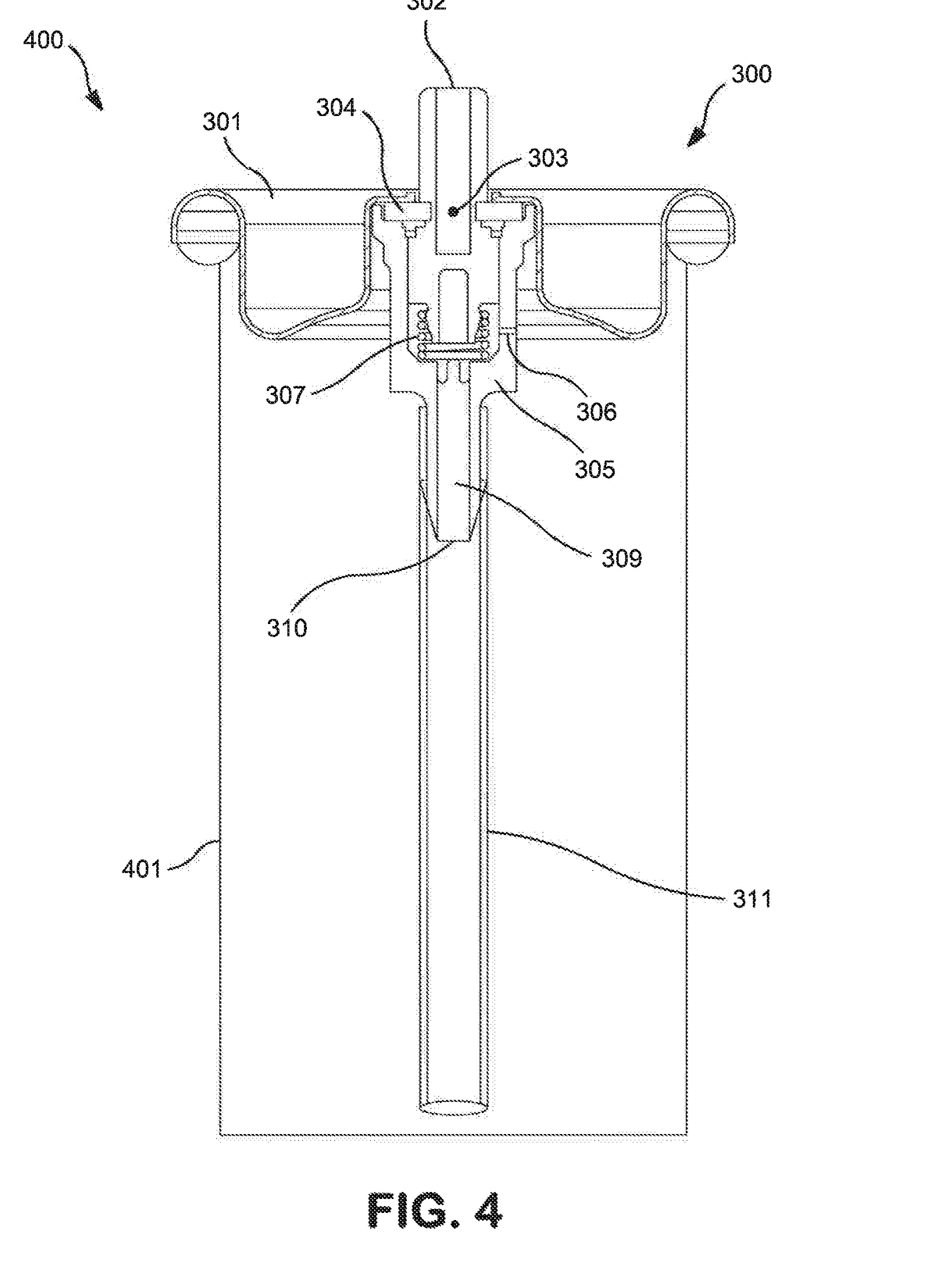
FIG. 4 is a cross-sectional side view of a spray delivery system according to another embodiment of the present disclosure utilizing the spray assembly of FIG. 3.

Regardless of which phase is being formed, the temperature can range from about 15° C. to about 40° C., such as from about 18° C. to about 35° C., such as from about 20° C. to about 30° C. After the separate phases are mixed as described above, the resulting base zinc oxide composition can then be filled into a spray container, such as an aerosol spray container. The container can then be sealed, after which the propellant can be introduced into the container, such as via a valve. The container can be filled with the propellant at a pressure ranging from about 130 psi to about 230 psi, such as from about 140 psi to about 220 psi, such as from about 150 psi to about 210 psi.

III. Spray Delivery System

Various aerosol spray containers can be used in conjunction with the sprayable zinc oxide composition to form a system for spraying the composition onto a surface such as skin. One embodiment of a spray delivery system contemplated by the present invention is described with reference to FIG. 1. The spray delivery system 100 can include a spray container 101 formed of metal or reinforced plastic. The spray container 101 has an upper opening into which a spray head 102 is fitted. The spray head or 102 is fixed onto the spray container 101 in such a manner that a flange 104 of the spray head is connected to a collar 103 formed around the edge of the upper opening in the spray container 101 by welding or other possible joining methods. This results in an airtight connection between the spray head 102 and spray container 101.

The spray head 102 is provided with a valve 105 that is retained by the flange 104. The valve 105 is kept closed in its normal condition by the energizing force of a spring 106, but it opens when the spray head 102 is pressed. The spray head 102 further has a spray nozzle 107 which communicates with the valve 105 through a conduit pipe 108. Meanwhile, a dip tube 109 is connected to the valve 105 and extends to the bottom of the spray container 101. By pressing the spray head 102 downwardly against the spring 106, the valve 105 opens to form a fluid passage from the lower end port of the dip tube 109 to the spray nozzle 107 through the valve 105 and conduit pipe 108.

The sprayable zinc oxide composition 110 as discussed above can be charged into the spray container 101. Then, by pressing the spray head 102, the sprayable zinc oxide composition is discharged in the form of a fine mist from the spray nozzle 107 through the aforementioned fluid passage by the pressure associated with the propellant that is substantially homogeneously dispersed in the sprayable zinc oxide composition 110.

Another embodiment of a spray delivery system is described with reference to FIGS. 2A, 2B, 3, and 4. Because of the use of zinc oxide particles, it is possible that the sprayable zinc oxide composition could clog some spray delivery systems. For instance, standard aerosol spray delivery systems often utilize an actuator (spray button) not intended for delivering compositions containing high concentrations of particulate material such as the zinc oxide particles of the present invention. Such actuators often utilize a mechanical break-up insert to finely atomize sprayable compositions containing low levels of particulates. For instance, the actuators can contain small channels to cause a swirling effect, resulting in a fine mist spray. However, when sprayable compositions containing higher amounts of particulate material are utilized, the particulate material, such as zinc oxide particles or any other active agent particles, can clog the actuator and prevent an even spray from the container. As such, the spray delivery system of the present invention represented by FIGS. 2A, 2B, 3, and 4 does not include the aforementioned actuator channels and is free from a mechanical break-up insert. Instead, the spray delivery system utilizes a valve and stem system where the stem design allows for automatic wiping of the stem inside the valve as the valve is sprayed, which prevents the buildup of solids inside the valve, thus minimizing the risk of clogging. In addition, the valve includes a valve orifice having a diameter that is large enough such that the zinc oxide particles and other particulates of the sprayable zinc oxide composition do not clog inside the container and such that an even mist can be achieved. Further, the valve includes a vapor tap to allow for enhanced blending of the propellant vapor during spraying and to prevent the buildup of particulates inside the valve. The addition of the vapor tap also results in a more uniform delivery of the sprayable composition from the delivery system. The vapor tap also allows for an increased weight percentage of propellant to be utilized, which helps to create a drier, less runny product when delivered to the surface of the skin. Further, the vapor tap creates a spray that feels warmer because it helps to volatilize the propellant and solvents before the composition reaches the surface of the skin.

The spray system is discussed in more detail below in reference to FIGS. 2A, 2B, 3, and 4. FIG. 2A shows a front view of a non-mechanical breakup actuator 200 that can be used in a spray delivery system according to one embodiment of the present disclosure. The actuator 200 is a component that can be used to depress a stem component of a valve assembly to initiate introduction of the sprayable zinc oxide composition, as is discussed in more detail below in reference to FIGS. 3 and 4. The actuator 200 includes a locking ring 201, an insert 202, and a dome 203. The locking ring 201 keeps the actuator from being depressed inadvertently. The actuator dome 203 can contain the insert 202, and the insert 202 can determine the spray characteristics of the sprayable zinc oxide composition. The insert 202 of FIGS.

2A and 2B is a non-mechanical breakup insert. The insert 202 defines an opening 204 from which the sprayable zinc oxide composition of the present invention can exit the actuator, and the opening is hereinafter referred to as the actuator orifice or exit orifice 204. The exit orifice 204 can have a diameter selected based on the particle size of the particulate components in the sprayable zinc oxide composition such that the particles and other components of the sprayable zinc oxide composition can be sprayed from the exit orifice 204 without causing clogging of the spray delivery system. Further, by selectively controlling the diameter of the exit orifice 204, the size of the resulting spray pattern can also be influenced. For instance, too small of a diameter can result in a very narrow spray pattern, while too large of a diameter can result in a spray pattern that is too wide, resulting in overspray into the surrounding environment other than the surface to be sprayed, such as clothing, bedding, etc. For instance, the exit orifice 204 can have a diameter ranging from about 0.3 millimeters to about 0.6 millimeters, such as from about 0.35 millimeters to about 0.55 millimeters, such as from about 0.4 millimeters to about 0.5 millimeters. FIG. 2B is a cross-sectional side view of the actuator of FIG. 2A, which shows the arrangement of the exit orifice 204 in relation to the insert 202 positioned inside the dome 203. The exit orifice is connected to a stem 302 of a valve assembly via an exit path 205, which is discussed in more detail in FIG. 3.

Turning now to FIGS. 3 and 4, a cross-sectional side view of a spray delivery system that includes a spray valve assembly 300 and mounting cup 301 that can be used in conjunction with the actuator 200 of FIGS. 2A and 2B is shown. The actuator 200 is connected to the valve assembly 300 by exit path 205 as shown in FIG. 2B. The spray valve assembly 300 includes a housing or body 305 that holds the stem 302, a stem gasket 304, and a spring 307. A dip tube 311 is also attached to the housing 305 via a tail pipe 309. The mounting cup 301 holds the spray valve assembly 300 together and can be crimped onto a container 401 to provide a seal. Generally, when the actuator 203 (see FIGS. 2A and 2B), which is disposed above the mounting cup 301, is depressed against the spring 307, the stem 302 of the valve assembly 300 moves downward, opening the seal between the stem gasket 303 and stem 302, such that a stem orifice 303 in the stem 302 passes below the stem gasket 304. This results in the propellant component of the sprayable zinc oxide composition forcing the base zinc oxide composition up the dip tube 311 through a tailpipe orifice 310, into the valve body 305. A vapor tap 306 formed in the valve body 305 supplies additional propellant to the valve body 305 and helps to mix the liquid base zinc oxide composition and propellant in the valve body 305, which can result in a more homogeneous distribution and reduce the risk of clogging of any particles, such as zinc oxide particles. The vapor tap 306 also keeps the base zinc oxide composition out of the valve body 305 when at rest due to the vapor pushing the base zinc oxide composition down, and also functions to prevent product settling. Once the sprayable zinc oxide composition (i.e., the substantially homogeneously blended propellant and base zinc oxide composition) reaches the stem through the stem orifice 303, it then passes through the exit path 205, and out the exit orifice 204 as a fine mist that does not clog the spray delivery system 400.

The dimensions of the various components can be selected to further minimize the risk of clogging. For instance, the stem 302 can have a diameter of from about 3 millimeters to about 5.5 millimeters, such as from about 3.5 millimeters to about 5 millimeters, such as from about 4 millimeters to about 4.5 millimeters. Meanwhile, the stem orifice 303 can have a diameter of from about 0.5 millimeters to about 0.75 millimeters, such as from about 0.55 millimeters to about 0.7 millimeters, such as from about 0.6 millimeters to about 0.65 millimeters. Additionally, the tailpiece orifice 310 can have a diameter of from about 0.75 millimeters to about 2 millimeters, such as from about 1 millimeter to about 1.75 millimeters, such as from about 1.25 millimeters to about 1.5 millimeters. Further, the vapor tap 306 can have a diameter of from about 0.1 millimeters to about 0.5 millimeters, such as from about 0.15 millimeters to about 0.45 millimeters, such as from about 0.2 millimeters to about 0.4 millimeters. By selectively controlling the aforementioned dimensions, the propellant of the sprayable zinc oxide composition can remain substantially homogeneously distributed throughout the base zinc oxide composition to reduce settling of the zinc oxide particles, and the sprayable zinc oxide composition can leave the exit orifice 204 as a fine mist with less fly away and can be more evenly distributed than when, for instance, a mechanical actuator is utilized.

IV. Application of the Sprayable Zinc Oxide Composition

As a result of the combination of the type of spray delivery system utilized and the characteristics of the sprayable composition, a substantially uniform coating of the composition can be applied to a surface. For instance, the composition of the present invention can be applied to a surface of the skin for the treatment of various skin conditions or irritations such as diaper rash; dry skin; ulcers; superficial cuts, scrapes, wounds, and first degree burns; etc. Areas of skin that can be treated include the buttocks, particularly in the case of diaper rash/incontinent dermatitis, as well as the arms, elbows, hands, abdomen, back, sacrum, coccyx, hips, knees, feet, ankles, heels, etc. As the composition reaches the skin's surface, the propellant can evaporate, leaving a substantially uniform coating of the base zinc oxide composition on the skin. Further, the zinc oxide particles can be distributed throughout the coating in a substantially uniform manner. After the composition has been sprayed onto the skin in the form of a substantially uniform coating, the amount of zinc oxide present in the composition on the skin can range from about 0.25 wt. % to about 35 wt. %, such as from about 0.5 wt. % to about 30 wt. %, such as from about 1 wt. % to about 25 wt. %, such as from about 5 wt. % to about 15 wt. % based on the total weight of the resultant coating (e.g., the sprayable zinc oxide composition excluding the evaporated components such as the propellant).

The present invention may be better understood by reference to the following examples.

Example 1

A sprayable zinc oxide composition was formed from a base zinc oxide composition including a preservative phase, an oil phase, a water phase to which a propellant was added. First, to make the preservative phase of the base zinc oxide composition, a freezing point depressant was added to a beaker and agitated with a propeller. Next, preservatives were added to the beaker and mixing was initiated using a stirrer equipped with an anchor-type sidewipe agitator. Agitation was continued for at least 15 minutes until the solution was completely dissolved. The preservative phase was then set aside.

Next, to make the oil phase of the base zinc oxide composition, emollients were added to a separate beaker and agitated with a propeller to initiate mixing while maintaining a temperature between 20° C. and 23° C., after which the polyglyceryl-4 isostearate/cetyl dimethicone copolyol/hexyl laurate emulsifier was added, followed by the cetyl PEG/PPG-10/1 dimethicone emulsifier, the sorbitan oleate emulsifier, the polysorbate 80 emulsifier, and the octyldodecanol/octyldechyl xyloside/PEG-30 emulsifier. Mixing via agitation was continued, while maintaining a temperature between 20° C. and 25° C. Next, the silicone oil was added to the beaker, while maintaining a temperature between 20° C. and 23° C. A homogenizer was then used for agitation, using cooling water to maintain a temperature between 20° C. and 25° C., after which a conditioning agent was added. Agitation was continued for at least 15 minutes until the solution was completely dissolved, maintaining a temperature between 20° C. and 28° C. The resulting oil phase of the base zinc oxide composition had an HLB value between 6 and 7.

Next, the water phase of the base zinc oxide composition was prepared in a separate beaker. Water was added to the beaker while maintaining a temperature between 20° C. and 28° C. Mixing was initiated using a stirrer equipped with a stainless steel three propeller blade. A water-soluble conditioning agent was added to the beaker and mixing was continued for at least 15 minutes until all solids were dissolved. Then, the viscosity modifier containing hydroxyethyl acrylate/sodium acryloyldimethyl taurate copolymer, squalane, and polysorbate 60 was added to the beaker, and mixing was continued for at least 15 minutes.

To prepare the base zinc oxide composition emulsion, the oil phase beaker was maintained at a temperature between 20° C. and 25° C. The water phase was then slowly transferred to the oil phase beaker under homogenizer agitation, where the transfer time was at least 20 minutes. The homogenizer speed was increased as needed, while maintaining a temperature between 20° C. and 25° C. The resulting water-in-oil emulsion was then covered and mixed for at least 30 minutes. The preservative phase was then added to the beaker while continuing mixing for at least 15 minutes and maintaining a temperature of from 20° C. to 25° C. After ensuring that all powders were off the surface and increasing the mixing speed as needed, zinc oxide particles were added under homogenizer agitation and mixed for at least 5 minutes, increasing the speed as needed and maintaining a temperature of from 20° C. to 25° C. Then the viscosity modifier aluminum starch octenylsuccinate was added under homogenizer agitation and mixed for at least 5 minutes, increasing the speed as needed and maintaining a temperature of from 20° C. to 25° C. Thereafter, fragrance was added to the beaker under homogenizer agitation, and the emulsion was mixed for at least 15 minutes. The resulting base zinc oxide composition had an HLB value of 7.42.

After the base zinc oxide composition was formed, it was filled into an aerosol spray container, after which the container's valve was sealed or crimped to the top of the container. Then, HFO-1234ze propellant was pressure filled via the valve into the container at a pressure of about 200 pounds. The resulting sprayable zinc oxide composition was a substantially homogeneous blend of the propellant and the base zinc oxide composition, which contained 22 wt. % of the propellant and 78 wt. % of the base zinc oxide composition. The sprayable composition had a specific gravity of about 1.045. The weight percentages of the components used in the sprayable zinc oxide composition are summarized below in Table 1. Once sprayed on a surface (e.g., skin) as a substantially uniform coating, the composition contained 10.4 wt. % of zinc oxide particles due to evaporation of the propellant.

TABLE 1

Sprayable Zinc Oxide Composition Components
Sprayable Zinc Oxide Composition

| Component | Wt. % |
| --- | --- |
| HFO-1234ze | 22.00 |
| Zinc Oxide Particles | 8.11 |
| Polyglyceryl-4 Isostearate; Cetyl PEG/PPG-10/1 Dimethicone; Hexyl Laurate | 0.98 |
| Cetyl PEG/PPG-10/1 Dimethicone | 0.98 |
| Sorbitan Oleate | 0.43 |
| Polysorbate 80 | 0.35 |
| Octyldodecanol/Octyldodecyl Xyloside/PEG-30 Dipolyhydroxystearate | 3.12 |
| Aluminum Starch Octenylsuccinate | 2.34 |
| Hydroxyethyl Acrylate/Sodium Acryloyldimethyl Taurate Copolymer, Squalane, Polysorbate 60 | 0.78 |
| Silicone Oil | 15.60 |
| Water | 29.76 |
| Conditioning Agents | 1.95 |
| Fragrance | 0.16 |
| Freezing Point Depressant | 3.12 |
| Preservatives | 0.20 |
| Emollients | 10.14 |
| Total | 100.00 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A sprayable zinc oxide composition comprising a fluoro-olefin propellant, zinc oxide particles, one or more nonionic lipophilic emulsifiers, wherein the one or more nonionic lipophilic emulsifiers comprises a non-crosslinked dimethicone polyol and a sorbitan fatty acid ester, one or more nonionic hydrophilic emulsifiers, and water, wherein the weight ratio of the one or more nonionic lipophilic emulsifiers to the one or more nonionic hydrophilic emulsifiers ranges from about 15 to about 20, and wherein the one or more nonionic lipophilic emulsifiers have a hydrophilic to lipophilic balance (HLB) value greater than 2 and less than 8, wherein the composition has an HLB value ranging from 3 to 10.

2. The sprayable zinc oxide composition of claim 1, wherein the fluoro-olefin propellant has a first specific gravity and the composition has a second specific gravity, wherein the ratio of the first specific gravity to the second specific gravity is from about 0.7 to about 1.6.

3. The sprayable zinc oxide composition of claim 1, wherein the fluoro-olefin propellant has a specific gravity of from about 1.03 to about 1.3.

4. The sprayable zinc oxide composition of claim 1, wherein the composition has a specific gravity of from about 0.8 to about 1.3.

5. The sprayable zinc oxide composition of claim 1, wherein the fluoro-olefin propellant has a vapor pressure of less than about 60 psi at about 21° C.

6. The sprayable zinc oxide composition of claim 1, wherein the fluoro-olefin propellant has a molecular weight of greater than about 100 grams per mole.

7. The sprayable zinc oxide composition of claim 1, wherein the fluoro-olefin propellant is substantially homogeneously dispersed throughout the composition.

8. The sprayable zinc oxide composition of claim 1, wherein the fluoro-olefin propellant has the following general structure:

wherein where each R is independently fluorine, bromine, iodine, or hydrogen,
R' is $(CR_2)_n Y$,
Y is $CRF_2$, and
n is 0 or 1.

9. The sprayable zinc oxide composition of claim 1, wherein the fluoro-olefin propellant comprises 1,1,1,3-tetrafluoropropene.

10. The sprayable zinc oxide composition of claim 1, further comprising a carrier fluid.

11. The sprayable zinc oxide composition of claim 10, wherein the carrier fluid is a water-in-oil emulsion or an oil-in-water emulsion.

12. The sprayable zinc oxide composition of claim 1, wherein the composition comprises one or more viscosity modifiers.

13. The sprayable zinc oxide composition of claim 1, further comprising one or more emollients, conditioning agents, freezing point depressants, preservatives, or a combination thereof.

14. The sprayable zinc oxide composition of claim 1, wherein the sprayable zinc oxide composition has a viscosity of greater than about 1000 centipoise.

15. The sprayable zinc oxide composition of claim 1, wherein the composition comprises a substantially homogeneous distribution of zinc oxide particles.

16. The sprayable zinc oxide composition of claim 1, wherein less than about 3 wt. % of the zinc oxide particles in the composition settle when the composition is stored in a container at about 21° C. for 3 days.

17. The sprayable zinc oxide composition of claim 1, wherein the one or more nonionic lipophilic emulsifiers comprises octyldodecanol/octyldecyl xyloside/PEG-30 dipolyhydroxystearate.

18. A method of forming a sprayable zinc oxide composition comprising:
forming a base zinc oxide composition, wherein the base zinc oxide composition comprises zinc oxide particles, one or more nonionic lipophilic emulsifiers, wherein the one or more nonionic lipophilic emulsifiers comprises a non-crosslinked dimethicone polyol and a sorbitan fatty acid ester, one or more nonionic hydrophilic emulsifiers, and a carrier fluid comprising water, wherein the weight ratio of the one or more nonionic lipophilic emulsifiers to the one or more nonionic hydrophilic emulsifiers ranges from about 15 to about 20, and wherein the one or more nonionic lipophilic emulsifiers have a hydrophilic to lipophilic balance (HLB) value greater than 2 and less than 8, wherein the composition has an HLB value ranging from 3 to 10;
introducing the base zinc oxide composition into a spray container; and
injecting a hydrofluoro-olefin propellant into the container.

19. The method of claim 18, wherein the carrier fluid is formed by combining a water phase with an oil phase to form a water-in-oil emulsion.

20. The method of claim 19, further comprising adding one or more of the emulsifiers to the oil phase.

21. The method of claim 19, further comprising adding one or more viscosity modifiers to the composition.

22. The method of claim 21, wherein at least one viscosity modifier is added to the water phase.

23. The method of claim 18, wherein the propellant is substantially homogeneously dispersed throughout the composition.

24. The method of claim 18, wherein the zinc oxide particles are substantially homogeneously dispersed throughout the composition.

25. The method of claim 18, wherein the sprayable zinc oxide composition has a viscosity of greater than about 1000 centipoise.

26. The method of claim 18, further comprising adding one or more preservatives, emollients, skin conditioners, freezing point depressants, or a combination thereof to the composition.

27. The method of claim 18, wherein the fluoro-olefin propellant has a first specific gravity and the sprayable zinc oxide composition has a second specific gravity, wherein the ratio of the first specific gravity to the second specific gravity is from about 0.7 to about 1.6.

28. The method of claim 18, wherein the sprayable zinc oxide composition is formed at a temperature ranging from about 15° C. to about 40° C.

29. A method of applying a sprayable zinc oxide composition to a surface, comprising spraying the composition onto the surface to leave a coating thereon, wherein the composition comprises a fluoro-olefin propellant, zinc oxide particles, one or more nonionic lipophilic emulsifiers, wherein the one or more nonionic lipophilic emulsifiers comprises a non-crosslinked dimethicone polyol and a sorbitan fatty acid ester, one or more nonionic hydrophilic emulsifiers, and water, wherein the weight ratio of the one or more nonionic lipophilic emulsifiers to the one or more nonionic hydrophilic emulsifiers ranges from about 15 to about 20, and wherein the one or more nonionic lipophilic emulsifiers have a hydrophilic to lipophilic balance (HLB) value greater than 2 and less than 8, wherein the composition has an HLB value ranging from 3 to 10.

30. The method of claim 29, wherein a substantially uniform coating is formed on the surface.

31. The method of claim 30, wherein the coating includes from about 1 wt. % to about 25 wt. % of zinc oxide particles based on the total weight of the coating.

32. The method of claim 29, wherein the surface is skin.

* * * * *